United States Patent [19]
Cooper et al.

[11] Patent Number: 6,127,916
[45] Date of Patent: Oct. 3, 2000

[54] FUEL SYSTEM LOW CURRENT RHEOSTAT

[75] Inventors: Richard O. Cooper, Bluffton; Terry R. Bloom, Middlebury; Curtis L. Holmes; John Zdanys, Jr., both of Elkhart, all of Ind.

[73] Assignee: CTS Corporation, Elkhart, Ind.

[21] Appl. No.: 08/853,080

[22] Filed: May 8, 1997

Related U.S. Application Data

[60] Provisional application No. 60/017,112, May 9, 1996.

[51] Int. Cl.$^7$ .................................................. H01L 10/48
[52] U.S. Cl. ........................... 338/190; 338/202; 338/33; 73/317
[58] Field of Search ...................................... 338/127, 171, 338/92, 95, 97, 190, 188, 185, 33, 202, 118, 191, 192, 193, 160, 162; 73/313, 317

[56] References Cited

U.S. PATENT DOCUMENTS

| | | | |
|---|---|---|---|
| 755,827 | 3/1904 | Yates et al. ............................... | 338/190 |
| 1,217,882 | 2/1917 | Roma ....................................... | 338/33 |
| 1,522,355 | 1/1925 | Roma ....................................... | 338/33 |
| 1,769,732 | 7/1930 | Becker ..................................... | 338/190 |
| 2,632,830 | 3/1953 | Aust et al. ............................... | 338/171 |
| 3,613,042 | 10/1971 | Leerkamp et al. . | |
| 3,614,704 | 10/1971 | Fujii et al. . | |
| 3,965,454 | 6/1976 | Puerner ................................... | 338/174 |
| 4,032,881 | 6/1977 | Singleton . | |
| 4,146,322 | 3/1979 | Shimizu et al. ......................... | 338/127 |
| 4,318,075 | 3/1982 | Pudelko et al. . | |
| 4,352,084 | 9/1982 | Graves et al. ........................... | 338/127 |
| 4,500,866 | 2/1985 | Romann et al. . | |
| 4,642,602 | 2/1987 | Maisch et al. .......................... | 338/162 |
| 4,694,272 | 9/1987 | Maisch ................................... | 338/138 |
| 4,931,764 | 6/1990 | Gaston . | |
| 4,994,752 | 2/1991 | Hata ....................................... | 338/202 |
| 5,051,719 | 9/1991 | Gaston et al. . | |
| 5,746,088 | 5/1998 | Sawert . | |

FOREIGN PATENT DOCUMENTS

| | | |
|---|---|---|
| 0310467 | 4/1989 | European Pat. Off. . |
| 0493339 | 7/1992 | European Pat. Off. . |
| 2613478 | 10/1988 | France . |
| 2048495 | 12/1980 | United Kingdom . |

*Primary Examiner*—Karl Easthom
*Attorney, Agent, or Firm*—Mark P. Bourgeois; Michael Starkweather; Jack Friedman

[57] ABSTRACT

A fuel level indicator system that utilizes a resistor card having an arc-shaped resistive path with a first set of spaced apart conductor lines and an arc-shaped resistive ink material overlying the first set of conductor lines. The first conductor lines are formed at an angle with respect to a radial line drawn from the center of the resistive path arc. The resistor card also has an arc-shaped continuously solid conductor base and a second set of spaced apart conductor lines extending from the base at an angle with respect to a radial line drawn from the center of the arc-shaped conductor base. The system includes a wiper assembly having a pair of spaced apart arms. Each arm has a plurality of parallel fingers extending from one end. One of the fingers on a first arm engages a conductor line on the resistive path and a second finger on the first arm engages an adjacent conductor line along the resistive path. A first finger on the second arm engages a conductive line on the conductive path; and a second finger engages an adjacent conductor line on the conductive path. The wiper assembly is constructed and arranged to provide rotational movement along the arc-shaped conductive path and arc-shaped resistive path. The system also has a float with an extending lever that is connected to the wiper assembly to produce rotational movement of the wiper assembly as the float moves.

2 Claims, 2 Drawing Sheets

FUEL SYSTEM LOW CURRENT RHEOSTAT

This application claims the benefit of provisional application Ser. No. 60/017,112, filed on May 9, 1996, entitled "FUEL SYSTEM LOW CURRENT RHEOSTAT."

BACKGROUND OF THE INVENTION

1. Field of the Invention

The present invention relates to variable resistors and in particular to a ceramic resistor card for use in a transducer for converting a physical position into an electrical signal.

2. Description of the Related Art

Variable resistors are known for sensing parameters in a variety of applications. For example, the fuel level in an automobile tank is typically measured using a variable resistor having a sweep arm mechanically or electrically coupled to a float located in a fuel tank. The sweep arm position is determined by the level of fuel in the tank and the voltage value sensed across the variable resistor depends on the position of the sweep arm.

The variable resistor typically comprises a resistor card with metalized areas and thick film resistive ink. The thick film ink is deposited in precise areas to interconnect respective metalized areas. There is a wiper blade assembly having contact fingers thereon connected to the sweep arm. As the float raises and lowers according to the fluid level, the wiper contact fingers move along the resistor card in an arcuate path and make corresponding contact with the metalized areas. This results in a voltage change that generates a signal representative of the amount of fuel contained in the tank.

One problem with this type of system is that over the life of a vehicle it must go through thousands of cycles in a harsh environment. The card is often exposed to both fuel and dry conditions as the fluid level is decreased. In addition, the assembly is exposed to severe vibration resulting from the vehicle movement. The result is that wear occurs as the wiper contact fingers go back and forth over the metalizations and the electrical resistance of the metalization portions may increase and cause accuracy problems with the fuel reading. Additionally, the metalized portions may wear to the point that an open circuit results along some given or several metalization locations.

Mother problem in some systems is that small circuit breaks occur as the arm sweeps from one metalization portion to the next. These breaks can cause spikes in the electrical characteristics of the variable resistor. A filter may have to be placed in the circuitry to minimize the spiking problem. It is desirable to eliminate the spiking and therefore the need for any associated filters.

Related Art

Examples of patents related to the present invention are as follows, and each patent is herein incorporated by reference for the supporting teachings:

U.S. Pat. No. 3,613,042, is a variable resistance element with spaced rows of parallel tabs.

U.S. Pat. No. 4,032,881 is a resistance element with improved linearity and method of making the same.

U.S. Pat. No. 4,318,075 is a thick film potentiometer having a wiper track with conductor lines deposited in a parallel fashion.

U.S. Pat. No. 4,500,866 is a nonlinear potentiometer including an arcuate resistor pad connected to a plurality of parallel resistor pads by means of a plurality of conductor lines.

U.S. Pat. No. 4,931,764 is a low wear resistance card for use in a liquid fuel sender card.

U.S. Pat. No. 5,051,719 is a thick-film non-step resistor with accurate resistance characteristics.

The foregoing patents reflect the state of the art of which the applicant is aware and are tendered with the view toward discharging applicants' acknowledged duty of candor in disclosing information that may be pertinent in the examination of this application. It is respectfully stipulated, however, that none of these patents teach or render obvious, singly or when considered in combination, applicant's claimed invention.

SUMMARY OF THE INVENTION

It is a feature of the invention to provide a fuel level indicator system. The system uses a resistor card having an arc-shaped resistive path with a first set of spaced apart conductor lines and an arc-shaped resistive ink material overlying the first set of conductor lines. The first conductor lines are formed at an angle with respect to a radial line drawn from the center of the resistive path arc. The resistor card also has an arc-shaped continuously solid conductor base and a second set of spaced apart conductor lines extending from the conductor base at an angle with respect to a radial line drawn from the center of the arc-shaped conductor base.

An additional feature of the invention is to provide a device that includes a wiper assembly having two sets of spaced apart wiper contacts or fingers. One of the fingers in each set engages a first conductor line and a second finger contacts a second adjacent conductor line. The wiper assembly is constructed and arranged to provide rotational movement along both the arc-shaped conductive and resistive path. Aver feature of the invention is to provide a device that has a float and a lever extending from the float connected to the wiper assembly to produce rotational movement of the wiper assembly as the float moves.

The invention resides not in any one of these features per se, but rather in the particular combination of all of them herein disclosed and claimed. Those skilled in the art will appreciate that the conception, upon which this disclosure is based, may readily be utilized as a basis for the designing of other structures, methods and systems for carrying out the several purposes of the present invention. Further, the abstract is neither intended to define the invention of the application, which is measured by the claims, neither is it intended to be limiting as to the scope of the invention in any way.

Figure 1:
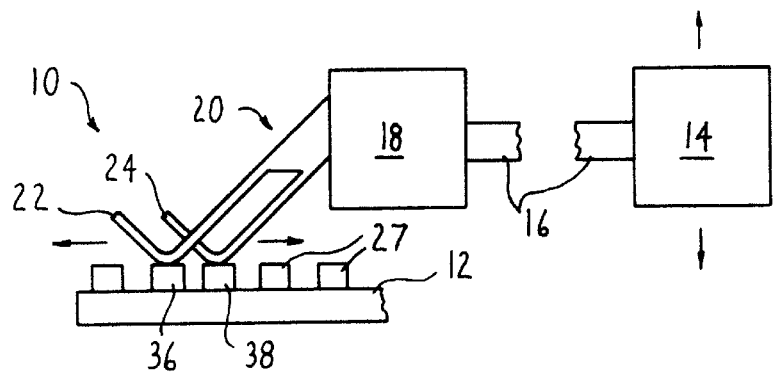
FIG. 1 is a representation of a fuel level detecting system.

It is noted that the drawings of the invention are not to scale. The drawings are merely schematic representations, not intended to portray specific parameters of the invention. The drawings are intended to depict only typical embodiments of the invention, and therefore should not be considered as limiting the scope of the invention. In the drawings, like numbering represents like elements between the drawings.

DETAILED DESCRIPTION OF THE PREFERRED EMBODIMENT

Figure 2:
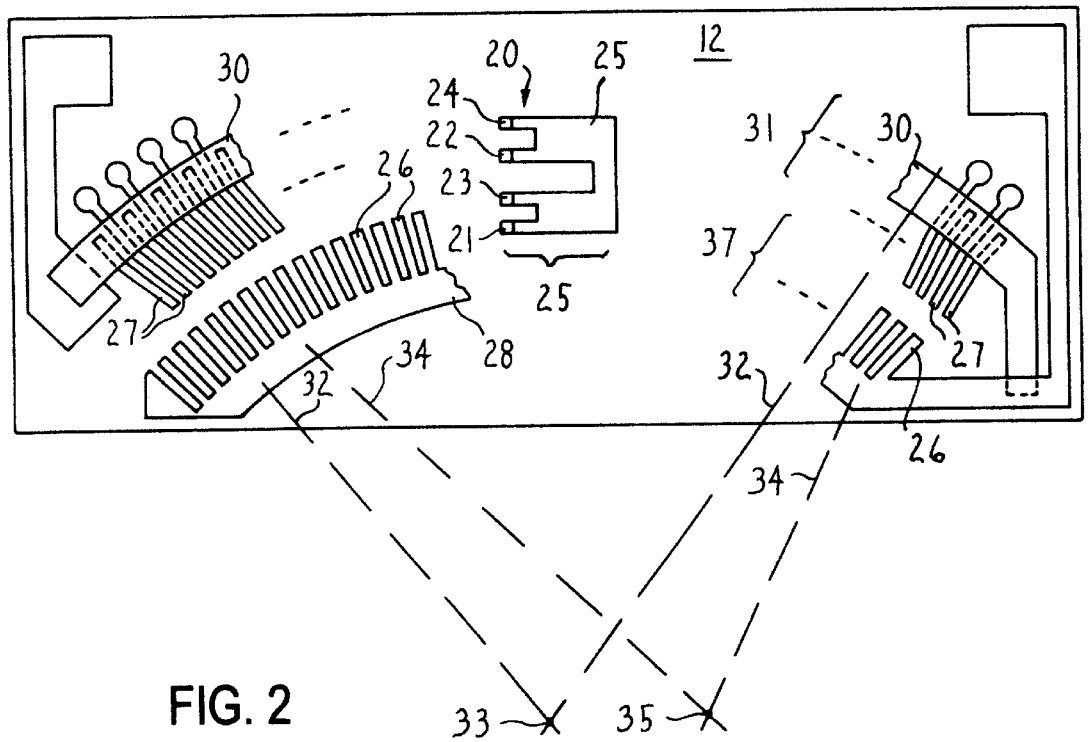
FIG. 2 is a top view of a ceramic resistor card for the fuel level detection system of FIG. 1.
Figure 3:
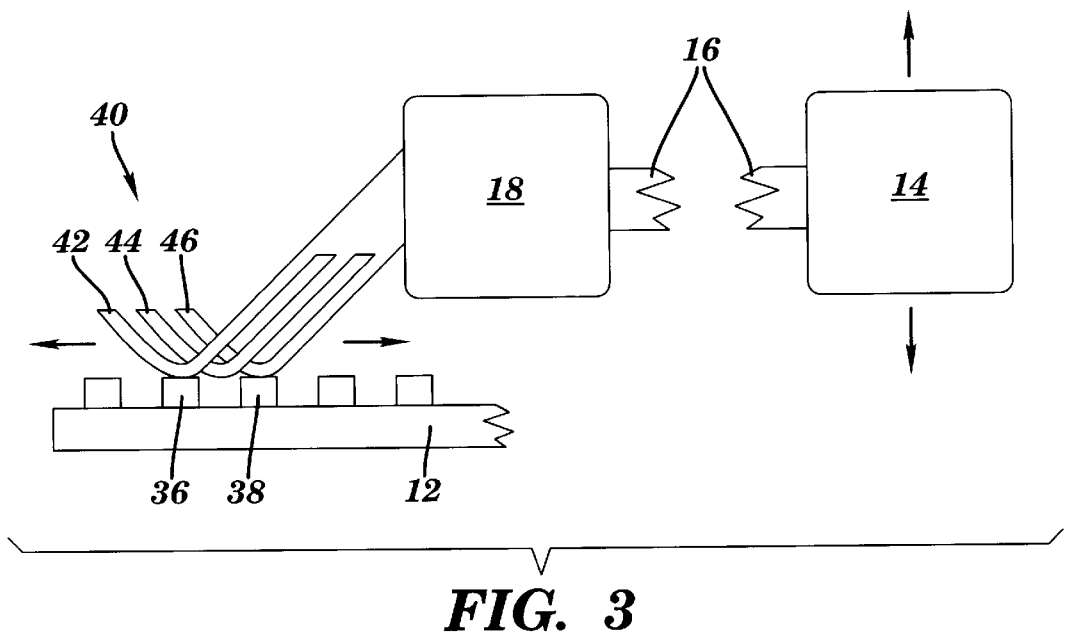
FIG. 3 represents an isometric view of a wiper arm having three fingers.
Figure 4:
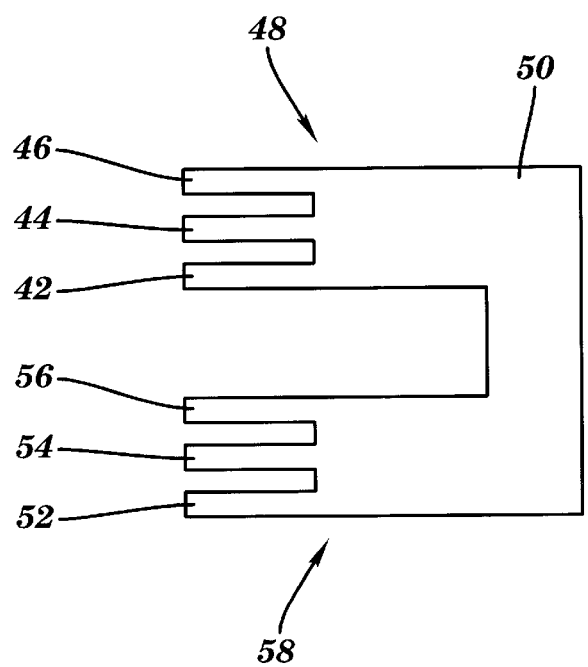
FIG. 4 represents a top view of a pair of wiper arms.

The present invention provides a fuel level detecting system 10 using a unique ceramic card 12 design. Regarding FIG. 1 and FIG. 2, there is fuel float 14 for floating in a fuel tank (not shown). The float 14 is coupled by a coupling 16 to a pivoting wiper linkage 18. Wiper blade assembly 20 is coupled to the pivoting wiper linkage 18 and has two wiper arms 25. Each arm 25 has conductive fingers 21 and 23, and 22 and 24, which are parallel to each other. A ceramic card 12 is used as a base for mounting resistive and conductive traces thereon. Radial lines 32 indicate the pivot point (or arcuate center) 33 used for determining the parallel arc-shaped design or path of the movable wiper blade assembly 20, arc-shaped resistor trace 30 and arc-shaped solid conductor trace 28. Accordingly, pivot point 33 represents the arcuate center of both arcs, i.e., arc-shaped resistor trace 30 and arc-shaped solid conductor trace 28. Radial lines 32 represent the set of all lines that can be drawn from the pivot point 33 to one of the respective arcs. Radial lines 34 indicate the common pivot point 35 of radially aligned conductor lines 26 and 27. The resistor trace 30 lies over a portion of each conductor line 27 to form a generally arc shaped resistive path 31. Conductor lines 26 extend from within the arc shaped resistive path 31. Conductor lines 26 extend from within an arc shaped continuously solid conductor base 28 to form a generally arc shaped conductor path 37. Fingers 22 and 24 are positioned to contact conductor lines 27 and fingers 21 and 23 are positioned to contact conductor lines 26 as the wiper blade assembly 20 rotates about point 33. Although the diagrams depict each wiper arm 25 having two fingers, it is recognized that three or more fingers could be utilized, and such variations fall within the scope of this invention. For example, FIG. 3 depicts a wiper arm configuration 40 with three fingers 42, 44 and 46. Similarily, FIG. 4 depicts a top view of a wiper arm configuration 50 comprising a pair of wiper arms 48 and 58, each having three fingers 42, 44, 46, and 52, 54, 56, respectively. The wiper arm configuration 50 depicted in FIG. 4 could replace the wiper arm configuration 25 depicted in FIG. 2.

In operation, as float 14 rises and lowers, coupling 16 moves wiper linkage 18 in a fashion to cause wiper blade assembly 20 to arcuately travel across conductor lines 26 and 27. The moving wiper blade assembly 20 is designed and oriented to have a make-before-break operation, ie. 22 and 24 in FIG. 1, make connection with a next conductor line 38 before breaking contact with a currently contacted conductor line 36. Because of the make-before-break design, never will there be an open circuit as a result of non-continuous contact between the fingers and conductor lines as the wiper assembly rotates about point 33.

Remarks About the Preferred Embodiment

One of ordinary skill in the art of designing and using potentiometers and ceramic cards will realize many advantages from using the preferred embodiment. For example, having the conductor lines 26 and 27 at a different angle than the angle of rotation and orientation for the fingers 21, 22, 23 and 24 creates a make-before-break connection therebetween. Thus, each of conductor lines 26 and 27 are formed at a non-zero angle with respect to radial lines 32.

An additional advantage of the preferred embodiment is that the fingers make contact with the conductor lines at an acute angle as opposed to a right angle. A smaller angle of impact will lessen the potential wear on the conductor lines from such impact over thousands of repetitive impacts.

Another advantage of the preferred embodiment is that the acute angle between the fingers and conductor lines prevents open circuit breaks as the wiper blade assembly sweeps across the ceramic card in the make-before-break design.

It is also noted that since the preferred embodiment uses conductor lines instead of a continuous conductive path there is less material used in making the conductor portions, which leads to an overall less expensive part.

It is noted that FIG. 1 does not illustrate all four contact fingers. It does illustrate the view looking along a radial line 34 as the fingers contact conductor lines 27. It is further noted that resistor trace 30 can be made of resistive ink material. It is also noted that radial lines 32 and 34 passing through the same conductor form an angle to each other.

Variations of the Preferred Embodiment

Although the illustrated embodiment discuss the arrangement of a fuel level sensor one skilled in the art will realize that the preferred embodiment would work with most any type of application besides fuel level sensing. For example, the sensor could be coupled to a computer joy stick or any device needed to sense relatively short positional changes.

Although coupling 16 is ambiguously illustrated, it is contemplated that coupling could be a mechanical lever, a cable, or even an electronically controlled position sensor actuator assembly.

Although wiper linkage 18 is ambiguously illustrated, it is contemplated that the linkage could be a rotatable housing with a pivot point fixed relative to point 33.

While the invention has been taught with specific reference to these embodiments, someone skilled in the art will recognize that changes can be made in form and detail without departing from the spirit and the scope of the invention. The described embodiments are to be considered in all respects only as illustrative and not restrictive. The scope of the invention is, therefore, indicated by the appended claims rather than by the description. All changes that come within the meaning and range of equivalency of the claims are to be embraced within their scope.

What is claimed and desired to be secured by patent is:
1. An indicator system, comprising:
   a resistor card having thereon an arc-shaped resistive path comprising a sot of spaced apart conductor lines and an arc-shaped resistor trace, said resistor trace having an arcuate center and overlying said set of conductor lines, each conductor line extending from within said trace to a common pivot point and at a non-zero angle with respect to a radial line drawn from said arcuate center; and
   a wiper assembly including an arm having a plurality of parallel fingers extending from one end so that one of said fingers on said arm engages a first conductor line adjacent said resistor trace and a second finger on said arm engages a second conductor line adjacent said resistor trace, said second conductor line being adjacent said first conductor line, said wiper assembly providing rotational movement of said fingers along said arc-shaped resistive path such that said second finger conductively contacts said second conductor line before said first finger breaks conductive contact with said first conductor line.
2. The indicator system of claim 1, wherein said resistor trace includes a resistive ink material.

* * * * *